(12) United States Patent
Islam et al.

(10) Patent No.: US 7,385,691 B2
(45) Date of Patent: *Jun. 10, 2008

(54) INTEGRATED MODULAR SYSTEM AND METHOD FOR ENHANCED RAMAN SPECTROSCOPY

(75) Inventors: M. Saif Islam, Sacramento, CA (US); Shih-Yuan Wang, Palo Alto, CA (US); Wei Wu, Mountain View, CA (US); Zhiyong Li, Palo Alto, CA (US); R. Stanley Williams, Redwood City, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 382 days.

This patent is subject to a terminal disclaimer.

(21) Appl. No.: 11/044,676

(22) Filed: Jan. 27, 2005

(65) Prior Publication Data

US 2006/0164636 A1    Jul. 27, 2006

(51) Int. Cl.
    *G01J 3/44* (2006.01)
    *G01N 21/65* (2006.01)
(52) U.S. Cl. ..................................... 356/301
(58) Field of Classification Search ............... 356/301
    See application file for complete search history.

(56) References Cited

U.S. PATENT DOCUMENTS

| | | | |
|---|---|---|---|
| 5,002,350 A | 3/1991 | Dragone | |
| 5,455,421 A | 10/1995 | Spears | |
| 6,380,531 B1 | 4/2002 | Sugihwo et al. | |
| 6,613,600 B2 | 9/2003 | Tran et al. | |
| 6,690,851 B1 | 2/2004 | Guilfoyle | |
| 6,726,763 B2 | 4/2004 | Lee et al. | |
| 6,775,308 B2 | 8/2004 | Hamster et al. | |
| 6,782,027 B2 | 8/2004 | Cox et al. | |
| 6,795,623 B2 | 9/2004 | Duan et al. | |
| 7,022,288 B1* | 4/2006 | Boss ..................... | 422/82.05 |
| 7,151,599 B2* | 12/2006 | Islam et al. ............ | 356/301 |

(Continued)

FOREIGN PATENT DOCUMENTS

GB    2408796    6/2005

(Continued)

OTHER PUBLICATIONS

Borgulova, J., et al., "Design of a Tunable RCE Photodetector for the 1550 nm Wavelength Range," ASDAM '98, 2$^{nd}$ International Conference on Advanced Semiconductor Devices and Microsystems, Smolenice Castle, Slovakia, Oct. 5-7, 1998, pp. 117-120.

(Continued)

*Primary Examiner*—F. L. Evans
*Assistant Examiner*—Jonathan Skovholt (57) ABSTRACT

Devices, systems, and methods for enhancing Raman spectroscopy and hyper-Raman are disclosed. A molecular analysis device for performing Raman spectroscopy comprises a substrate and a laser source disposed on the substrate. The laser source may be configured for emanating a laser radiation, which may irradiate an analyte disposed on a Raman enhancement structure. The Raman enhancement structure may be disposed on the substrate or apart from the substrate. The molecular analysis device also include a radiation receiver disposed on the substrate and configured for receiving a Raman scattered radiation, which may be generated by the irradiation of the analyte and Raman enhancement structure.

21 Claims, 5 Drawing Sheets

U.S. PATENT DOCUMENTS

| | | |
|---|---|---|
| 2004/0021860 A1 | 2/2004 | Gardner et al. |
| 2004/0142484 A1* | 7/2004 | Berlin et al. ............... 436/171 |
| 2005/0024634 A1* | 2/2005 | Barker et al. ............... 356/301 |

FOREIGN PATENT DOCUMENTS

| | | |
|---|---|---|
| WO | WO 00/43754 | 7/2000 |
| WO | WO 02/079821 | 10/2002 |
| WO | WO 2006/010367 | 2/2006 |
| WO | WO 2006/027581 | 3/2006 |

OTHER PUBLICATIONS

Emsley, Matthew K., et al., "High-Speed Resonant-Cavity-Enhanced Silicon Photodetectors on Reflecting Silicon-On-Isulator Substrates," IEEE Photonics Technology Letters, vol. 14, No. 4, Apr. 2002, pp. 519-521.

Emsley, Matthew K., et al., "Silicon Substrates With Buried Distributed Bragg Reflectors for Resonant Cavity-Enhanced Optoelectronics," IEEE Journal of Selected Topics in Quantum Electronics, vol. 8, No. 4, Jul./Aug. 2002, pp. 948-955.

Jiang, Jiang, et al., "Single Molecule Raman Spectroscopy at the Junctions of Large Ag Nanocrystals," J. Phys. Chem. B, vol. 107, No. 37, 2003, pp. 9964-9972.

Kelley, Anne Myers, et al., "Resonance Hyper-Raman Scattering from Conjugated Organic Donor-Acceptor "Push-Pull" Chromophores with Large First Hyperpolarizabilities," J. Am. Chem. Soc., vol. 125, No. 35, 2003, pp. 10520-10521.

Kishino, Katsumi, et al., "Resonant Cavity-Enhanced (RCE) Photodetectors," IEEE Journal of Quantum Electronics, vol. 27, No. 8, Aug. 1991, pp. 2025-2034.

Purica, M., et al., "Analysis and Optimization of the Bragg Reflector for Tunable Photodetector with Planar Mirror Optical Microcavity on Silicon Substrate," IEEE, 2003, pp. 155-158.

Smit, Meint K., et al., "PHASAR-Based WDM-Devices: Principles, Design and Applications," IEEE Journal of Selected Topics in Quantum Electronics, vol. 2, No. 2, Jun. 1996, pp. 236-250.

Yelin, Dvir, et al., "Multiphoton plasmon-resonance microscopy," Optics Express, vol. 11, No. 12, Jun. 16, 2003, pp. 1385-1391.

Song et al—"Photonic Devices Based on In-Plane Hetero Photonic Crystals"—Science vol. 300 No. 5625—Jun. 6, 2003.

* cited by examiner

INTEGRATED MODULAR SYSTEM AND METHOD FOR ENHANCED RAMAN SPECTROSCOPY

CROSS REFERENCE TO RELATED APPLICATIONS

The present application is related to concurrently filed U.S. patent application Ser. No. (200500097) entitled MONOLITHIC SYSTEM AND METHOD FOR ENHANCED RAMAN SPECTROSCOPY, and concurrently filed U. S. patent application Ser. No. (200402383) entitled INTEGRATED SYSTEM AND METHOD FOR TRANSVERSAL ENHANCED RAMAN SPECTROSCOPY.

FIELD OF THE INVENTION

The present invention relates to chemical analysis using Raman spectroscopy. More particularly, the present invention relates to integrated systems for enhancement of Raman spectroscopy combining a radiation source and Raman scattered radiation sensing. In addition, the present invention relates to hyper-Raman, where the excitation wavelength is approximately an integer multiple of the Raman wavelength.

BACKGROUND OF THE INVENTION

Raman Spectroscopy is a well-known spectroscopic technique for performing chemical analysis in the gas, liquid or solid phase. In conventional Raman Spectroscopy, high intensity monochromatic light from a light source, such as a laser, is directed onto an analyte to be chemically analyzed. The analyte may contain a single species of molecules or mixtures of different molecules. Furthermore, Raman Spectroscopy may be performed on a number of different molecular configurations, such as organic and inorganic molecules in crystalline or amorphous states.

For a system that does not have surface or nanostructure enhancement, the majority of the incident photons of the light are elastically scattered by the analyte molecule. In other words, the scattered photons have the same frequency, and thus the same energy, as the photons that were incident on the analyte. This is known as Rayleigh scattering. However, a small fraction of the photons (i.e., 1 in $10^7$ photons) are inelastically scattered by the unenhanced analyte molecule at a different optical frequency than the incident photons. The inelastically scattered photons are termed the "Raman scattered radiation" and may be scattered at frequencies greater than, but most are usually scattered at a frequency lower than, the frequency of the incident photons. When the incident photons collide with the molecules and give up some of their energy, the Raman scattered photons emerge with a lower energy and thus at a lower frequency. The lower energy Raman scattered photons are commonly referred to in Raman spectroscopy as the "Stokes radiation." A small fraction of the molecules are already in an energetically excited state and when the incident photons collide with the molecules, the Raman scattered photons emerge at a higher energy and thus at a higher frequency. The higher energy Raman scattered photons are commonly referred to in Raman spectroscopy as the "anti-Stokes radiation." Raman scattering can occur from the rotational, vibrational, or electronic states of the molecules.

The Stokes and the anti-Stokes Raman scattered photons are collected using optics, the different frequencies are dispersed spatially with some type of spectrometer, and the photons are registered by a detector, such as a photomultiplier, resulting in a spectral graph of intensity at a corresponding frequency (i.e., proportional to energy) for the Raman scattered photons. By plotting the intensity of the inelastically scattered Raman photons against frequency, a unique Raman spectrum, which corresponds to the particular analyte molecules, is obtained. This Raman spectrum may be used to identify chemical species, as well as other physical properties of the analyte. While conventional Raman Spectroscopy is suitable for bulk chemical analysis, it is not effective for surface studies because the signal from the bulk Raman scattered photons overwhelms any signal from Raman scattered photons near the surface.

In hyper-Raman spectroscopy, when excitation radiation impinges on an analyte molecule, a very small number of photons may be scattered at frequencies corresponding to the higher order harmonics of the excitation radiation, such as the second and third harmonics (i.e., twice or three times the frequency of the excitation radiation). Some of these photons may be Raman scattered photons with a frequency that is Raman-shifted relative to the frequencies corresponding to the higher order harmonics of the excitation radiation. Therefore, in Hyper-Raman spectroscopy, the incident excitation photons have approximately ½, ⅓, or ¼ the frequency of the Raman photons.

Due to the deficiencies with performing surface studies using conventional Raman Spectroscopy, another Raman Spectroscopy technique called Surface Enhanced Raman Spectroscopy (SERS), which is effective for performing surface studies, has been developed. In SERS, a monolayer or sub-monolayer amount of the molecules to be analyzed is adsorbed onto a specially roughened metal surface. Typically, the metal surface is made from gold, silver, copper, lithium, sodium, or potassium. Raman spectroscopy has also been used employing metallic nanoparticles or nanowires for the metal surface, as opposed to a roughened metallic surface, which is hereinafter referred to as Nano-Enhanced Raman Spectroscopy (NERS). The intensity of the Raman scattered photons from a collection of molecules adsorbed on such a surface is typically about $10^4$-$10^6$ greater than conventional Raman Spectroscopy from a similar number of molecules in a bulk specimen, and can be as high as $10^8$-$10^{14}$ for a single molecule adsorbed near two or more metal nanoparticles. Although not thoroughly understood, the selectivity of the surface Raman signal results from the presence of surface enhancement mechanisms and is mainly attributed to two primary mechanisms: electromagnetic enhancement and chemical enhancement, with the electromagnetic enhancement being the dominant mechanism. The enhanced electromagnetic field is highly dependent on the surface roughness features of the enhancement surface. The chemical enhancement is believed to be dependent on the altered electronic structure of the enhancement surface due to adsorption of the analyte. The enhanced electromagnetic field of the enhancement surface, which is adjacent to the analyte, irradiates the analyte, producing an enhanced Raman signal having a strength that is, in part, proportional to the square of the enhanced electromagnetic field. Thus, Raman spectroscopy may be used to study monolayers of materials adsorbed on metals, and even single molecules adsorbed near an appropriate metal nanostructure.

In a conventional Raman spectroscopy system, a spectrometer collects all radiation, including the Stokes radiation, anti-Stokes radiation, and the elastically scattered radiation, and provides a spectrum of the scattered radiation. The spectrum may then be used to identify the chemical species, as well as other physical properties, of the analyte.

Conventionally, the spectrometer may include various optical elements such as lenses, gratings, photomultipliers, and filters. While this arrangement may be flexible, it is often bulky, expensive, and requires significant user interaction to analyze a chemical species.

An integrated modular Raman spectroscopy analysis system, which integrates a laser light source and a scattered radiation dispersing and detection element, may be a smaller and less costly system. This integrated Raman spectroscopy analysis system may be easier to use and may be adaptable to detection of a predetermined set of molecules. In addition, an integrated Raman spectroscopy analysis system may integrate the Raman scattering enhancement structure (surface or nanostructure), creating a self-contained integrated Raman spectroscopy analysis system.

BRIEF SUMMARY OF THE INVENTION

The present invention, in a number of embodiments, includes devices for generating Raman scattered radiation, Surface Enhanced Raman Spectroscopy (SERS) systems, Nano-Enhanced Raman Spectroscopy (SERS) systems, and methods of performing SERS and NERS.

In one aspect of the present invention, a molecular analysis device comprises a substrate and a laser source disposed on the substrate. The laser source is configured for emanating a laser radiation, which may irradiate an analyte disposed on a Raman enhancement structure. The molecular analysis device also includes a radiation receiver disposed on the substrate. The radiation receiver is configured for sensing at least two unique wavelengths of the Raman scattered radiation, which may be generated by the irradiation of the analyte and Raman enhancement structure.

Other embodiments of the present invention include methods for performing Raman spectroscopy. One method of performing Raman spectroscopy comprises generating laser radiation from a laser source disposed on a substrate, disposing an analyte over at least a portion of a Raman enhancement structure, and irradiating the analyte and the Raman enhancement structure with the laser radiation to generate Raman scattered radiation. The method further includes sensing at least two unique wavelengths of the Raman scattered radiation with at least two wavelength-specific sensors disposed on the substrate.

In yet another embodiment, a method of performing Raman spectroscopy comprises generating a laser radiation from a laser source disposed on a substrate, disposing an analyte over at least a portion of a Raman enhancement structure, and irradiating the analyte and the Raman enhancement structure with the laser radiation to generate a Raman scattered radiation. The method further includes dispersing the Raman scattered radiation into at least two unique wavelengths and sensing the at least two unique wavelengths with at least two sensors disposed on the substrate.

BRIEF DESCRIPTION OF THE SEVERAL VIEWS OF THE DRAWINGS

While the specification concludes with claims particularly pointing out and distinctly claiming that which is regarded as the present invention, the advantages of this invention can be more readily ascertained from the following description of the invention when read in conjunction with the accompanying drawings in which:

DETAILED DESCRIPTION OF THE INVENTION

The present invention, in a number of embodiments, includes structures and devices for use in Surface Enhanced Raman Spectroscopy (SERS) systems, Nano-Enhanced Raman Spectroscopy (NERS) systems, and methods of performing SERS and NERS. Systems that may incorporate SERS and NERS techniques are generally referred to as employing Enhanced Raman Spectroscopy (ERS). As shown in the figures and described in further detail below, molecular analysis structures and molecular analysis devices of the present invention incorporate a laser source with a radiation receiver on a substrate. In some embodiments, a Raman enhancement structure may be disposed on the substrate, while in other embodiments the Raman enhancement structure may be separate from the molecular analysis device. In addition, the sensitivity of Raman spectroscopy systems of the present invention may be enhanced by the type of surface on the Raman enhancement structure to enable more accurate and sensitive detection of chemical species and other physical properties of the sample being analyzed, including single molecule detection. Furthermore, the Raman spectroscopy systems of the present invention may be employed as an analytical instrument for detecting specific chemicals.

Figure 1:
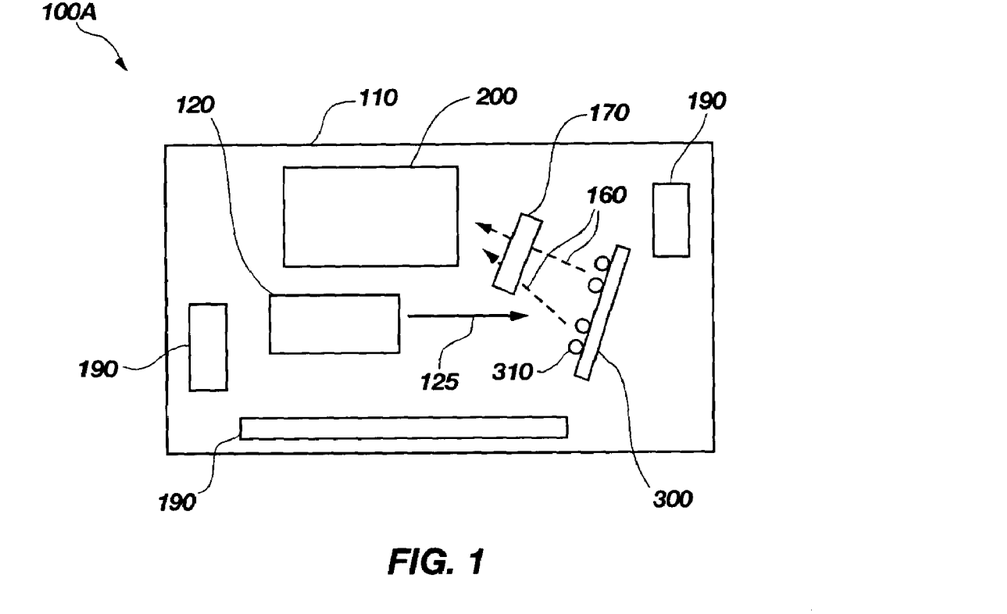
FIG. 1 is a top view of an exemplary molecular analysis device including a Raman enhancement structure disposed on a substrate.

FIG. 1 illustrates an exemplary embodiment of a molecular analysis device 100A employing Raman spectroscopy. The molecular analysis device 100A includes the substrate 110, the laser source 120 disposed on the substrate 110, the radiation receiver 200 disposed on the substrate 110, and the Raman enhancement structure 300 disposed on the substrate 110. An optional filter 170 may also be disposed on the substrate 110 between the Raman enhancement structure 300 and the radiation receiver 200. The molecular analysis device 100A may also include other optional substrate components 190. This embodiment may be used as a self-contained Raman spectroscopy analysis system, wherein an analyte 310 may be disposed on the Raman enhancement structure 300. In operation, the laser source 120 emits a laser radiation 125 to irradiate the analyte 310 on the Raman enhancement structure 300. The combined irradiation of the Raman enhancement structure 300 and the analyte 310 may generate Raman scattered radiation 160. The Raman scattered radiation 160 may be detected as a variety of wavelengths by the radiation receiver 200, as explained more fully below.

Figure 2:
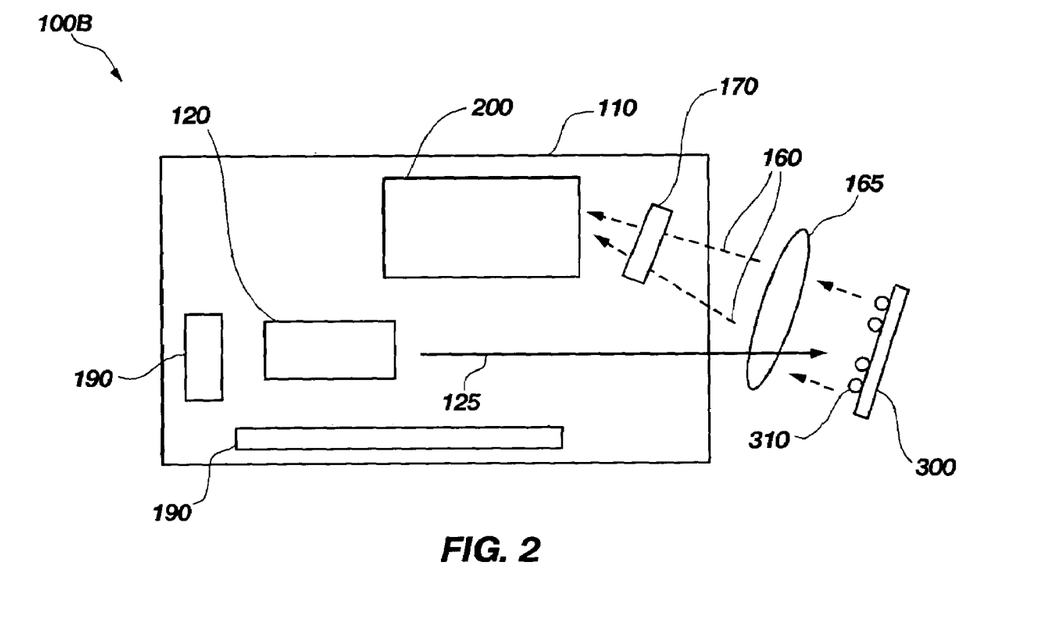
FIG. 2 is a top view of an exemplary molecular analysis device including the Raman enhancement structure disposed apart from the substrate.

Similarly, FIG. 2 illustrates another exemplary embodiment of a molecular analysis device, identified as 100B. In the embodiment of FIG. 2, the molecular analysis device 100B includes the substrate 110, the laser source 120 disposed on the substrate 110, and the radiation receiver 200 disposed on the substrate 110. However, in the embodiment of FIG. 2, the Raman enhancement structure 300 may be separated from the molecular analysis device 100B. An optional filter 170 may also be disposed on the substrate 110 between the Raman enhancement structure 300 and the radiation receiver 200. The molecular analysis device 100B may also include other optional substrate components 190. This embodiment may be used in a Raman spectroscopy analysis system, wherein it may be desirable to use a variety of Raman enhancement structures 300 or other optional external components 165, while still using the molecular analysis device 100B as the laser source 120 and the radiation receiver 200. In addition, optional external components 165 may be employed.

FIG. 2, by way of example, illustrates a lens as an optional external component 165, which may be used to focus the Raman scattered radiation 160 near the radiation receiver 200 on the substrate 110. Many other optional external components 165 are possible and encompassed by the scope of the invention, such as, for example, filters, mirrors, collimators, and lenses. The Raman enhancement structure 300 may be disposed external from the substrate 110 at a position where the laser radiation 125 may irradiate the analyte 310 on the Raman enhancement structure 300, which may generate Raman scattered radiation 160. The Raman scattered radiation 160 may be detected as a variety of wavelengths by the radiation receiver 200, as explained more fully below.

The Raman enhancement structure 300, whether disposed on the substrate 110 or as a separate component, may be used to effect the electromagnetic enhancement of the Raman signal, chemical enhancement of the Raman signal, or both. If disposed on the substrate 110, Raman enhancement structure 300 may be associated with substrate 110 by chemically bonding or merely disposing the same on the substrate 110, followed by weak bonding thereto or, alternatively, no bonding at all.

As used herein, the term "Raman enhancement structure" means any structure configured and formed of a material that may produce chemical enhancement of the Raman signal, electromagnetic enhancement of the Raman signal, or both. Exemplary materials for formation of the Raman enhancement structure 300 include gold, silver, copper, aluminum, chromium, lithium, sodium, potassium, or any other suitable material that may produce chemical enhancement of the Raman signal, electromagnetic enhancement of the Raman signal, or both.

It has been shown that a relatively rough surface enhances the amount of Raman scattered radiation 160 that may emanate from the Raman enhancement structure 300 when an analyte 310 disposed on the Raman enhancement structure 300 is irradiated. As a result, the Raman enhancement structure 300 may be formed as a single monolithic layer, possibly with a roughened surface, or the Raman enhancement structure 300 may comprise one or more discrete particles.

As one or more discrete particles, the Raman enhancement structure 300 may have a variety of exemplary configurations, such as, nanowires (e.g., a rod shaped configuration), nanodots, nanoparticles (including employing a single nanoparticle), or metallic particles in a colloidal suspension. It is currently preferred to employ at least two silver nanoparticles spaced apart, such that an analyte 310 molecule may be draped therebetween. The aforementioned nanostructures for the Raman enhancement structure 300 may be formed by chemical vapor deposition (CVD), molecular beam epitaxy (MBE), atomic layer deposition (ALD), or any other known technique for depositing the Raman enhancement structure 300.

The substrate 110 may be any suitable substrate 110 for bearing the laser source 120, the radiation receiver 200, and, if present, the Raman enhancement structure 300. In addition, if optional substrate 110 components are present, the substrate 110 may be selected for its properties of directing and modifying either optical signals, electrical signals, or both optical signals and electrical signals. By way of example, conventional silicon substrates as well as Group III-V materials, such as gallium arsenide, and indium phosphide may be desirable. In addition, the substrate 110 may be a circuit board using a material, such as, for example, FR4 circuit board material.

It may be desirable to include other optional substrate components 190 to create an enhanced Raman spectroscopy analysis system. By way of example, Application Specific Integrated Circuits (ASIC), microprocessors, microcontrollers, digital signal processors, and discrete components may be useful. In addition, optical components such as collimators, lenses, filters, waveguides and resonant cavities may be useful. Furthermore, nanowire-type sensor arrays may be desirable for verifying the presence and composition of some analytes 310.

The laser source 120 may be a conventional laser diode, which emits a laser radiation 125 with a wavelength that is effective for Raman spectroscopy analysis. By way of example, an edge-emitting laser diode is illustrated in the exemplary embodiments. However, it is understood that other laser diode implementations are possible and encompassed by the scope of the invention, such as, for example, a Vertical Cavity Surface Emitting Laser (VCSEL).

The radiation receiver 200 may be implemented as a plurality of wavelength-specific sensors 210 or may be implemented as a wavelength demultiplexer 240 with radiation sensors 290.

Figure 3:
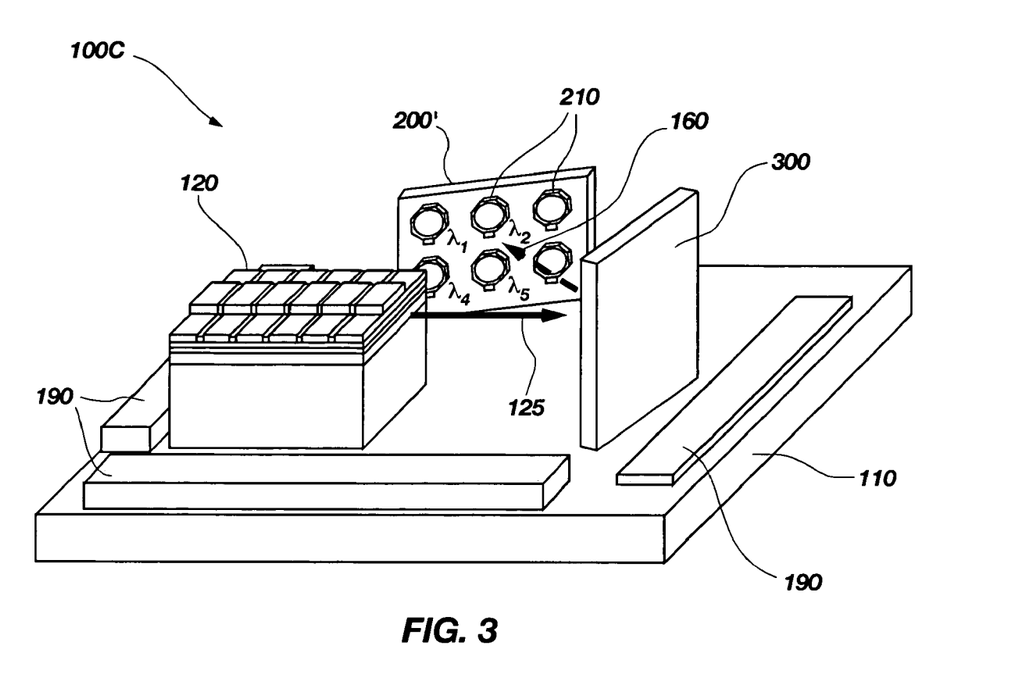
FIG. 3 is a three dimensional view of an exemplary embodiment of a molecular analysis device including the Raman enhancement structure on the substrate and an exemplary embodiment of a radiation receiver including wavelength-specific sensors.
Figure 4:
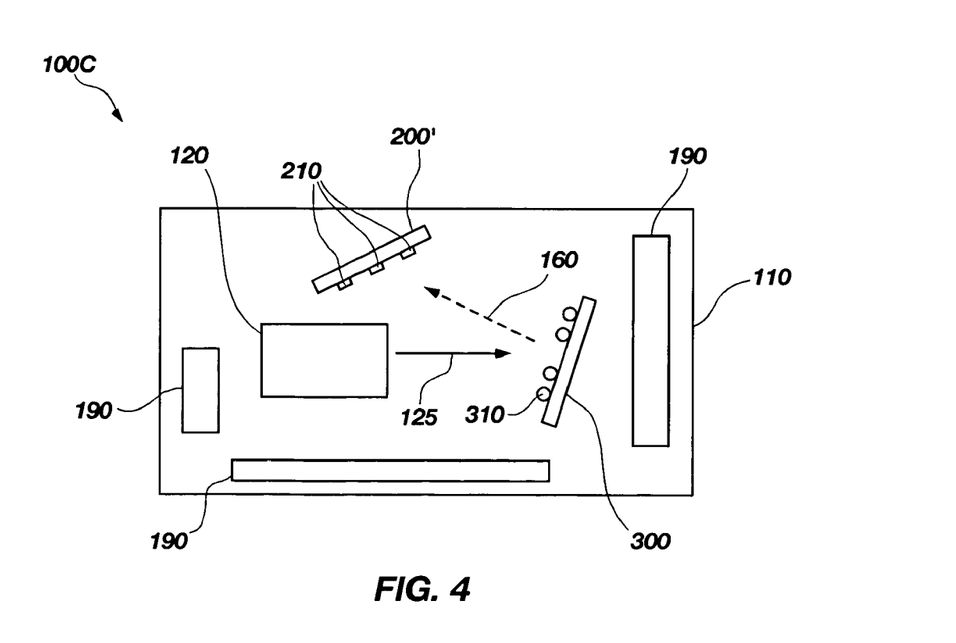
FIG. 4 is a top view of the exemplary embodiment of FIG. 3.

An exemplary radiation receiver 200' implemented as a plurality of wavelength-specific sensors 210 is illustrated in FIGS. 3 and 4. Each wavelength-specific sensor 210 may be tuned to detect a specific wavelength. As a result, the radiation receiver 200' may be configured to simultaneously detect a variety of wavelengths of Raman scattered radiation 160 such that, with the plurality of wavelength-specific sensors 210, a Raman spectrum may be obtained.

The Raman spectrum may be used to determine specific analytes 310. In this fashion, an inexpensive molecular analysis device 100C may be developed to detect a predetermined set of analytes 310. Other molecular analysis devices 100C may include wavelength-specific sensors 210 tuned to other frequencies for detecting a different set of analytes 310.

Figure 5:
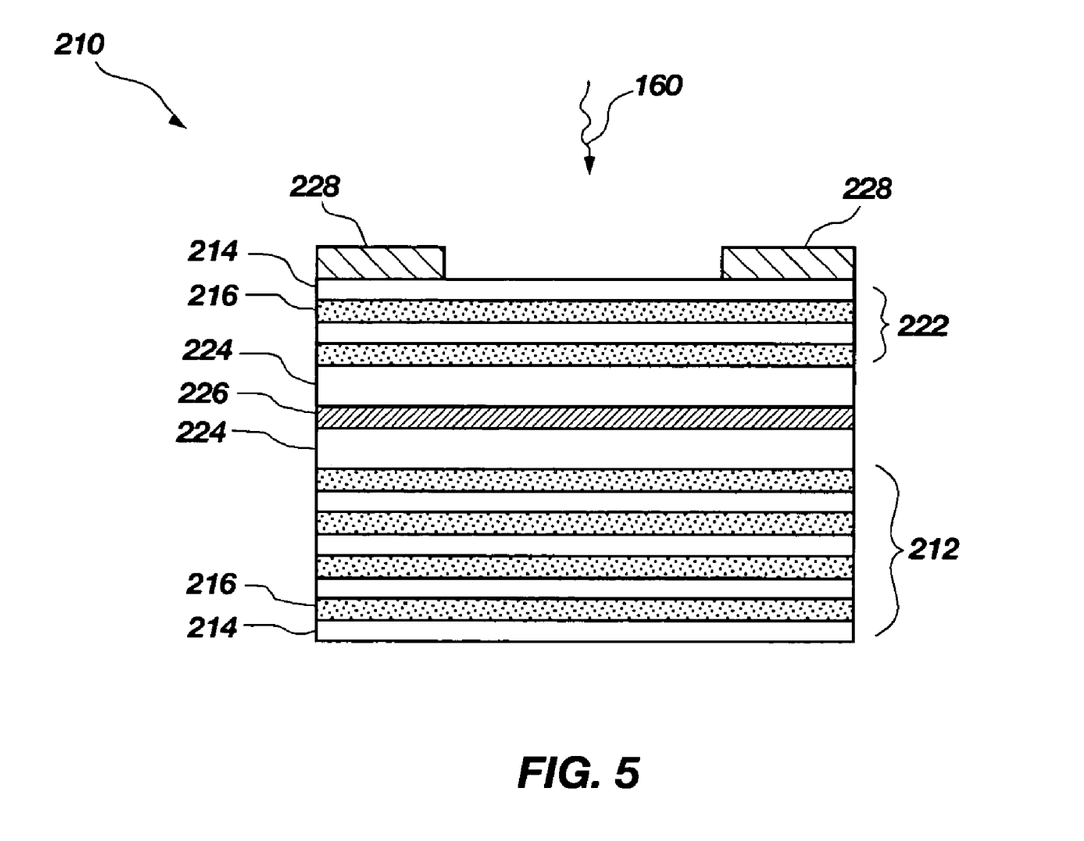
FIG. 5 is a cross-sectional view of an exemplary resonant cavity enhanced photodiode.

The wavelength-specific sensors 210 may be, for example, a plurality of Resonant Cavity Enhanced (RCE) photodiodes. An exemplary RCE photodiode 210 is shown in FIG. 5. RCE photodiodes 210 include a resonant cavity formed between a top reflector 222 and a bottom reflector 212. The resonant cavity includes an active region 226, which may include multiple quantum wells. The active region 226 is configured to create an electrical potential by absorbing photons within the active region 226. By placing the active absorption region within a resonant cavity, an RCE photodiode 210 may be much more sensitive to radiation than a conventional photodiode, due to the light trapping caused by the resonant cavity. In addition, if the resonant cavity, top reflector 222, and bottom reflector 212 are configured for a specific wavelength, the RCE photodiode 210 has a much greater sensitivity for radiation near the specific wavelength.

In a conventional RCE photodiode 210 configuration, one of either the top reflector 222 or the bottom reflector 212 is doped with a p-type material and the other mirror is doped with an n-type-material. This doping creates a diode such that the absorption of photons by the active material in the active region 226 is converted to electrons and an electrical current proportional to the intensity of the radiation received by the RCE photodiode 210. This electrical current may be directed to other optional substrate components 190 or may be directed to electrical components apart from the molecular analysis device 100C for further analysis.

The top reflector 222 and bottom reflector 212 may be structures, such as, for example, distributed Bragg reflectors (also referred to as Bragg Mirrors) or distributed Bragg gratings.

For example, the bottom Bragg reflector 212 may be doped to create an n-type material and the top Bragg reflector 222 may be doped to create a p-type material. The resulting structure may conventionally be referred to as a P-I-N diode. In this example, the bottom Bragg reflector 212 may be connected to a ground voltage potential, while the top Bragg reflector 222 may be connected to a signal for carrying the generated electrical current.

Bragg reflectors may be formed in a number of ways using a variety of materials configured as alternating layers; one layer with a low refractive index and the other layer with a high refractive index. Each layer can be configured with a thickness of about one quarter of an odd multiple of the specific wavelength to be resonantly trapped by the RCE photodiode 210. For example, the layers may be configured with a thickness of ¼ of a wavelength or ¾ of a wavelength. The resulting Bragg reflector may also be referred to as a quarter-wave stack. As an example, a Bragg reflector may be formed from alternating layers of GaAs (gallium arsenide) and AlGaAs (aluminum gallium arsenide). Another suitable material combination for forming Bragg reflectors includes alternating layers formed respectively from silicon and silicon dioxide. Implementing a larger number of alternating pairs in a Bragg reflector results in a higher refractive index. About thirty layers may create a reflectivity as high as 99.99%. In a conventional RCE photodiode 210, the bottom reflector 212 may have a very high reflectivity. The top reflector 222 conventionally has a lower reflectivity to allow radiation to enter the resonant cavity while also reflecting a large percentage of the radiation back inside the resonant cavity once inside.

As shown in FIG. 5, the bottom Bragg reflector 212 may be formed from alternating first layers 214 and second layers 216. The top Bragg reflector 222 is similarly formed from alternating first layers 214 and second layers 216. Between the top Bragg reflector 222 and the bottom Bragg reflector 212, a quantum well active region 226 may be formed. The active region 226 may be separated from the top Bragg reflector 222 and the bottom Bragg reflector 212 by spacer layers 224. The spacer layers 224 may be formed with a thickness that places the active region 226 substantially near an optimum placement between the two reflectors to create a high Q factor optical cavity for resonantly trapping the specific wavelength to be detected.

Figure 6:
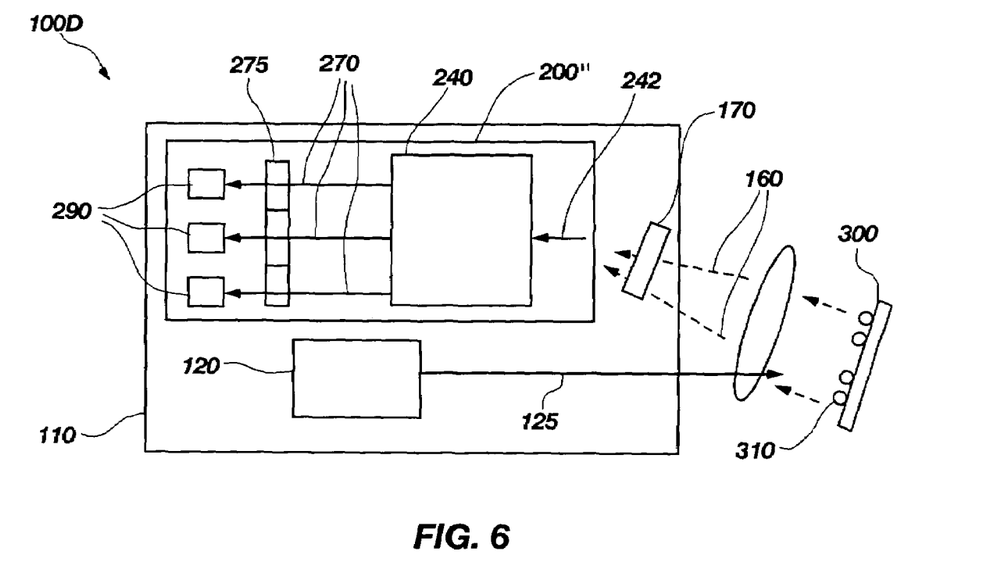
FIG. 6 is a top view of an exemplary embodiment of a molecular analysis device including the Raman enhancement structure apart from the substrate and an exemplary embodiment of the radiation receiver including a wavelength demultiplexer.

Rather than using wavelength-specific sensors 210, another embodiment of the present invention, as illustrated in FIG. 6, includes a wavelength demultiplexer 240 as part of the radiation receiver 200". In the exemplary embodiment of the molecular analysis device 100D shown in FIG. 6, the Raman enhancement structure 300 is apart from the molecular analysis device 100D and the molecular analysis device 100D includes the laser source 120 and the radiation receiver 200". The FIG. 6 radiation receiver 200" includes a wavelength demultiplexer 240, transmission waveguides 270, an optional filter 170, optional optical amplifiers 275, and radiation sensors 290. By demultiplexing the Raman scattered radiation 160, the unique wavelengths exiting the wavelength demultiplexer 240 may be sensed by simple photodiodes responsive to a broad range of wavelengths rather than the RCE photodiodes 210 of the FIG. 4 embodiment. Transmission waveguides 270 direct the unique wavelengths 260 from the wavelength demultiplexer 240 to the radiation sensors 290.

If desired, optical amplifiers 275 may be implemented in the transmission waveguides 270 to amplify the unique wavelengths 260 since simple photodiodes may not have the resonant enhancement characteristics of RCE photodiodes 210.

Figure 7:
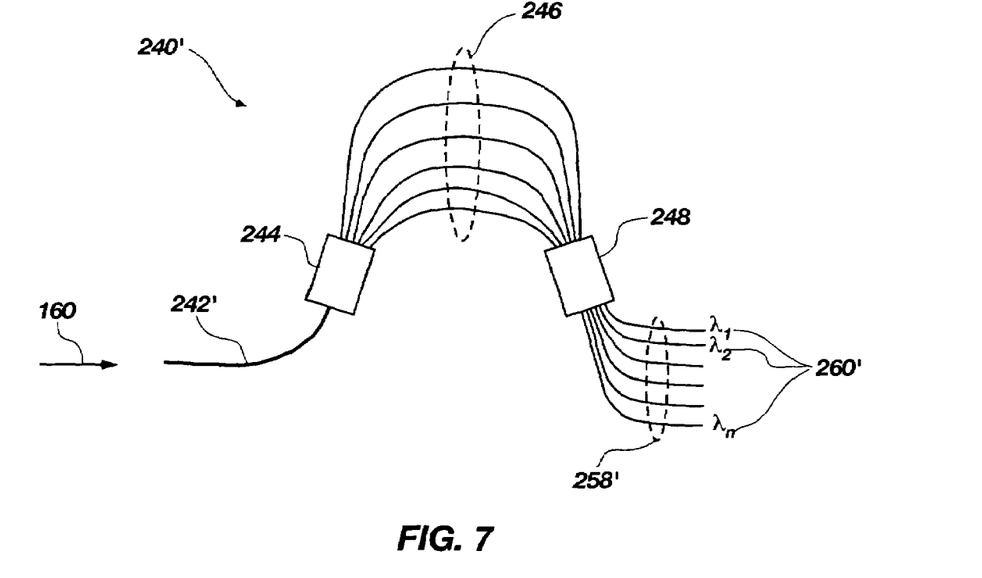
FIG. 7 is a top view of an exemplary wavelength demultiplexer employing an arrayed waveguide grating.
Figure 8:
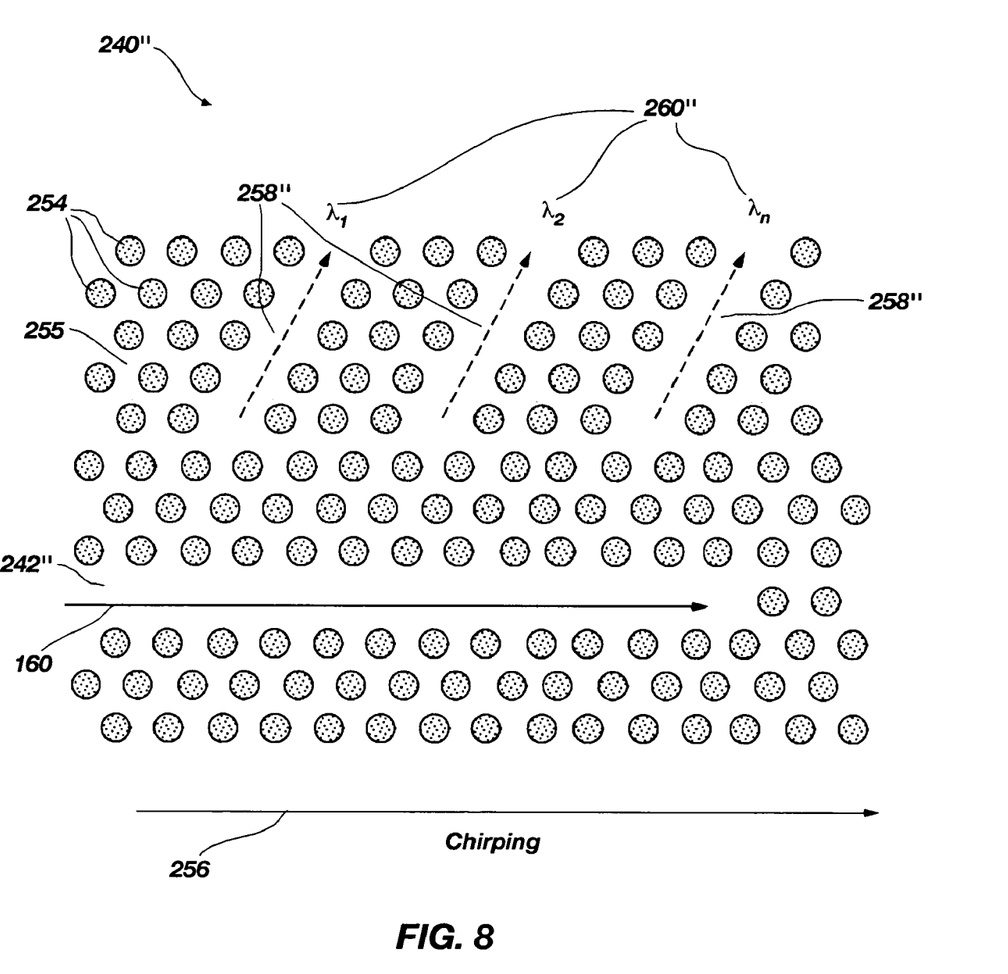
FIG. 8 is a top view of an exemplary wavelength demultiplexer employing a chirped photonic crystal.

Exemplary embodiments of a wavelength demultiplexer 240 include an Arrayed Waveguide Grating (AWG) element 240' (FIG. 7) and a chirped photonic crystal 240" (FIG. 8). An AWG 240' may operate as a wavelength multiplexer and a wavelength de-multiplexer. An exemplary AWG is shown in FIG. 7. A root waveguide 242' guides the Raman scattered radiation 160 to a free propagation region 244 where the Raman scattered radiation 160 may diverge to an array of waveguides 246. The array of waveguides 246 is configured such that the optical path lengths of adjacent waveguides differ by substantially near an integer multiple of the central wavelength. The individual waveguides of the array of waveguides 246 arrive at an output aperture 248 where they are recombined. Receiver waveguides (also referred to as wavelength-specific waveguides 258') are placed at a proper position along an image plane in the output aperture 248 such that spatial separation of the various wavelengths achieves the wavelength de-multiplex function. As a result, each wavelength-specific waveguide 258' carries a unique wavelength 260' out of the AWG 240'.

Another exemplary wavelength demultiplexer 240, illustrated in FIG. 8, includes a chirped photonic crystal 240". A conventional two-dimensional photonic crystal material may be formed by periodically dispersing rods or columns 254 of a material of one refractive index within a matrix 255 having a different refractive index. Two-dimensional photonic crystals 240" exhibit periodicity in only two dimensions (i.e., the directions perpendicular to the length of the rods or columns 254), but no periodicity is exhibited in the direction parallel to the length of the columns 254. The photonic crystal 240" material, as shown in a top view in FIG. 8 creates a highly refractive behavior in the two dimensions of the photonic crystal 240" material. As a result, a waveguide may be created in the photonic crystal 240" by introducing a series of defects. The defects may be formed by removing or failing to form one or more columns 254 along a path for the radiation to follow. Alternatively, the defects may be formed as air gaps or as spatially confined areas of a different material such as glass or epoxy. The defects in the photonic crystal 240" material create a waveguide along the path of the defects due to the high reflectivity in the plane perpendicular to the columns 254. For example, in the exemplary embodiment of FIG. 8, a root waveguide 242" and three wavelength-specific waveguides 258" are shown.

In addition to a conventional periodic arrangement of columns 254 forming the photonic crystal 240", a photonic crystal 240" may be formed with a "chirped" arrangement. As a chirped photonic crystal 240", the periodicity (i.e. spacing between columns 254) changes along the chirped axis 256. This chirping is useful in creating wavelength-specific waveguides 258".

As shown in FIG. 8, the photonic crystal 240" includes a chirped axis 256 substantially in a horizontal direction. In other words, the columns 254 become farther apart (or closer together) as the radiation travels from left to right along the chirped axis 256. A root waveguide 242" may carry the Raman scattered radiation 160 along this chirped axis 256. Wavelength-specific waveguides 258" may tap off at various points along the root waveguide 242". Only radiation of wavelengths substantially matching the periodicity of the columns 254 at that point along the chirped axis 256 will pass through the photonic crystal 240" and enter the wavelength-specific waveguide 258" at that location.

In operation of a Raman spectroscopy system, and referring to FIGS. 1, 2, 4, and 6, the laser source 120 irradiates the Raman enhancement structure 300 and analyte 310 producing a Raman enhancement effect therein (i.e., chemical, electromagnetic, or both). In other words, irradiation of the Raman enhancement structure 300 and analyte 310 by radiation impinging on the Raman enhancement structure 300 and analyte 310, in part, produces a strong electromagnetic field in the Raman enhancement structure 300. Because the electromagnetic field is adjacent to the analyte 310, the analyte 310 is, in turn, irradiated by a very strong electromagnetic field. The irradiation of the analyte 310 by the enhanced field from the Raman enhancement structure 300 produces the aforementioned Stokes, anti-Stokes, or combined (Stokes/anti-Stokes) Raman scattered photons (also referred to as Raman scattered radiation 160) that are characteristic of the particular analyte 310 being analyzed. Because the intensity of the Raman scattered photons is, in part, proportional to the square of the electromagnetic field that irradiates the analyte 310, the enhancement effect from the Raman enhancement structure 300 may increase the intensity of the Raman signal by as much as $10^{14}$.

If used for hyper-Raman spectroscopy, when excitation radiation impinges on an analyte molecule, a small number of photons may be scattered at frequencies corresponding to the higher order harmonics of the excitation radiation, such as the second and third harmonics (i.e., twice or three times the frequency of the excitation radiation). Some of these photons may be Raman scattered photons with a frequency that is Raman-shifted relative to the frequencies corresponding to the higher order harmonics of the excitation radiation. Therefore, in hyper-Raman spectroscopy, as examples and not limitations of higher order harmonics, the incident excitation photons may have approximately ½, ⅓, or ¼, the frequency of the Raman photons.

This hyper-Raman excitation has the added advantage that the excitation frequency and Rayleigh scattered radiation at the excitation frequency may be easily filtered out from the Raman signal frequency by an inexpensive optical filter 170. In this invention, we define ERS to include Raman, hyper-Raman and higher multiple excitation photons.

For illustration of a specific example, and not a limitation, the excitation photon may have a wavelength of about 980 nm, and the Raman signal may have wavelengths of about 490 nm. As a result, the filter 170 may be configured to substantially filter out the radiation at and near the 980 nm wavelength, while passing the shorter wavelengths. Alternatively photodiodes comprising GaN/InGaN/AlGaN, which are transparent to 980 nm but detect frequencies near 490 nm may be used.

Some of the Raman scattered radiation 160 may be detected by the radiation receiver 200. With a wavelength-specific sensor 210 embodiment (FIGS. 4-6), each sensor detects a somewhat different wavelength and converts the intensity detected into an electrical signal. Similarly, with a wavelength demultiplexer 240 embodiment (FIGS. 6-8), the wavelength demultiplexer 240 separates the Raman scattered radiation 160 into a plurality of unique wavelengths 260, which are sensed by simple radiation sensors 290. The radiation sensors 290 convert the intensity detected into electrical signals.

The electrical signals from either embodiment may be directed to electronic equipment located apart from the molecular analysis device 100 (i.e., devices 100A, 100B, 100C, or 100D) or may be directed to other optional substrate components 190 for development of a Raman spectrum, which may be used to identify a specific analyte 310.

Although the foregoing description contains many specifics, these are not to be construed as limiting the scope of the present invention, but merely as providing certain exemplary embodiments. Similarly, other embodiments of the invention may be devised which do not depart from the spirit or scope of the present invention. The scope of the invention is, therefore, indicated and limited only by the appended claims and their legal equivalents, rather than by the foregoing description. All additions, deletions, and modifications to the invention, as disclosed herein, which fall within the meaning and scope of the claims, are encompassed by the present invention.

What is claimed is:

1. A molecular analysis device, comprising:
   a substrate;
   a laser source disposed on the substrate, the laser source configured for irradiating an analyte disposed on a Raman enhancement structure with a laser radiation to produce a Raman scattered radiation; and
   a radiation receiver disposed on the substrate and comprising at least two wavelength-specific radiation sensors, wherein the radiation receiver is configured for sensing at least two unique wavelengths of the Raman scattered radiation, and each wavelength-specific sensor is configured for sensing one of the at least two unique wavelengths of the Raman scattered radiation.

2. The device of claim 1, wherein the laser radiation comprises a wavelength that is an integer multiple of a wavelength substantially near the Raman scattered radiation.

3. The device of claim 2, further comprising a filter disposed between the Raman enhancement structure and the radiation receiver, the filter configured for substantially filtering out radiation substantially near the wavelength of the laser radiation.

4. The device of claim 1, wherein the at least two wavelength-specific sensors comprise resonant cavity enhanced photodiodes.

5. The device of claim 1, wherein the at least two wavelength-specific sensors are arranged in a matrix.

6. A molecular analysis device, comprising:
   a substrate;

a laser source disposed on the substrate the laser source configured for irradiating an analyte disposed on a Raman enhancement structure with a laser radiation to produce a Raman scattered radiation; and a radiation receiver disposed on the substrate and comprising at least two radiation sensors, wherein the radiation receiver is configured for sensing at least two unique wavelengths of the Raman scattered radiation, wherein the Raman enhancement structure is disposed on the substrate and the Raman enhancement structure is configured to be irradiated by the laser radiation and to produce Raman scattered radiation receivable by the radiation receiver.

7. The device of claim 1, wherein the Raman enhancement structure comprises a metallic material selected from the group consisting of gold, silver, copper, aluminum, chromium, lithium, sodium, and potassium.

8. The device of claim 7, wherein the Raman enhancement structure is substantially roughened to increase a surface enhancement effect of the Raman scattered radiation.

9. The device of claim 1, wherein the Raman enhancement structure comprises a plurality of nanostructures including a metallic material, wherein the plurality of nanostructures are selected from the group consisting of nanodots and nanowires.

10. The device of claim 9, wherein the metallic material is selected from the group consisting of gold, silver, copper, aluminum, chromium, lithium, sodium, and potassium.

11. The device of claim 1, wherein the Raman enhancement structure comprises a colloid containing metallic particles, wherein the metallic particles are selected from the group consisting of gold, silver, copper, aluminum, chromium, lithium, sodium, and potassium.

12. A method of performing Raman spectroscopy, comprising:

generating a laser radiation from a laser source disposed on a substrate;

disposing an analyte over at least a portion of a Raman enhancement structure;

irradiating the analyte and the Raman enhancement structure with the laser radiation to generate a Raman scattered radiation; and sensing at least two unique wavelengths of the Raman scattered radiation with at least two wavelength-specific sensors disposed on the substrate.

13. The method of claim 12, further comprising generating a wavelength of the laser radiation that is an integer multiple of a wavelength substantially near the Raman scattered radiation.

14. The method of claim 13, further comprising filtering the Raman scattered radiation to substantially remove radiation substantially near the wavelength of the laser radiation.

15. The method of claim 12, further comprising selecting resonant cavity enhanced photodiodes as the at least two wavelength-specific sensors.

16. The method of claim 12, further comprising arranging the at least two wavelength-specific sensors in a matrix.

17. The method of claim 12, further comprising disposing the Raman enhancement structure on the substrate.

18. The method of claim 12, wherein disposing the analyte comprises disposing at least one molecule of the analyte.

19. The method of claim 12, further comprising selecting the Raman enhancement structure to comprise a metallic material selected from the group consisting of gold, silver, copper, aluminum, chromium, lithium, sodium, and potassium.

20. The method of claim 12, wherein the Raman enhancement structure comprises a colloid including metallic particles selected from the group consisting of gold, silver, copper, aluminum, chromium, lithium, sodium, and potassium.

21. The method of claim 12, wherein the Raman enhancement structure comprises at least one particle in the form of a nanodot or a nanorod.

* * * * *

UNITED STATES PATENT AND TRADEMARK OFFICE
CERTIFICATE OF CORRECTION

PATENT NO. : 7,385,691 B2
APPLICATION NO. : 11/044676
DATED : June 10, 2008
INVENTOR(S) : M. Saif Islam et al.

It is certified that error appears in the above-identified patent and that said Letters Patent is hereby corrected as shown below:

On the face page, in field (75), in "Inventors", in column 1, line 5, delete "Redwood City," and insert -- Portola Valley, --, therefor.

In column 11, line 1, in Claim 6, after "substrate" insert -- , --.

Signed and Sealed this

Fourteenth Day of July, 2009

JOHN DOLL
*Acting Director of the United States Patent and Trademark Office*